United States Patent [19]
Schieber

[11] 3,960,496
[45] June 1, 1976

[54] CORROSION PROBE DEVICE FOR BOILER GASES

[75] Inventor: John R. Schieber, Holland, Pa.

[73] Assignee: Betz Laboratories, Inc., Trevose, Pa.

[22] Filed: Oct. 30, 1975

[21] Appl. No.: 627,171

[52] U.S. Cl. .................................. 23/253 C; 73/86
[51] Int. Cl.[2] .......................................... G01N 17/00
[58] Field of Search ............ 23/253 C, 230 C; 73/86

[56] References Cited
UNITED STATES PATENTS

| | | | |
|---|---|---|---|
| 2,864,252 | 12/1958 | Schaschl | 23/253 C X |
| 3,166,932 | 1/1965 | Ellison | 73/86 |
| 3,222,920 | 12/1965 | Marsh et al. | 73/86 |
| 3,627,493 | 12/1971 | Manley | 23/253 C |
| 3,861,876 | 1/1975 | Robertson et al. | 23/253 C X |

Primary Examiner—Robert M. Reese
Attorney, Agent, or Firm—Steven H. Markowitz; Alexander D. Ricci

[57] ABSTRACT

Apparatus for determining corrosion or deposition rate of corrosive constituents in the flue gases of a boiler system. A probe loop has a coolant circulating therethrough wherein the loop includes a removable specimen that can be tested for deposition or corrosion rate. The coolant recirculates through the loop to maintain the surface temperature of the specimen substantially constant approximating the maximum corrosion temperature. Coolant is fed to the probe loop by a coolant tank which includes a liquid coolant reservoir in a lower portion thereof and a gas chamber for gaseous coolant in an upper portion thereof. The gas pressure within the gas chamber can be varied so as to vary the boiling point temperature of the liquid coolant. The gas chamber is connected to the lower end of a condenser coil which has a variable heat transfer area. Between the gas chamber and the condenser coil is located a contact bed to enhance the contact of condensed coolant and gaseous coolant. To enhance the flow of the coolant through the loop by nucleate boiling the return run and supply runs of the loop are inclined upwardly.

28 Claims, 5 Drawing Figures

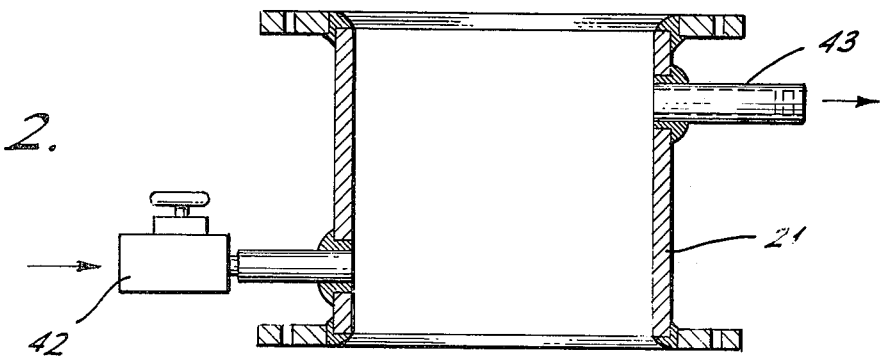
FIG. 2.
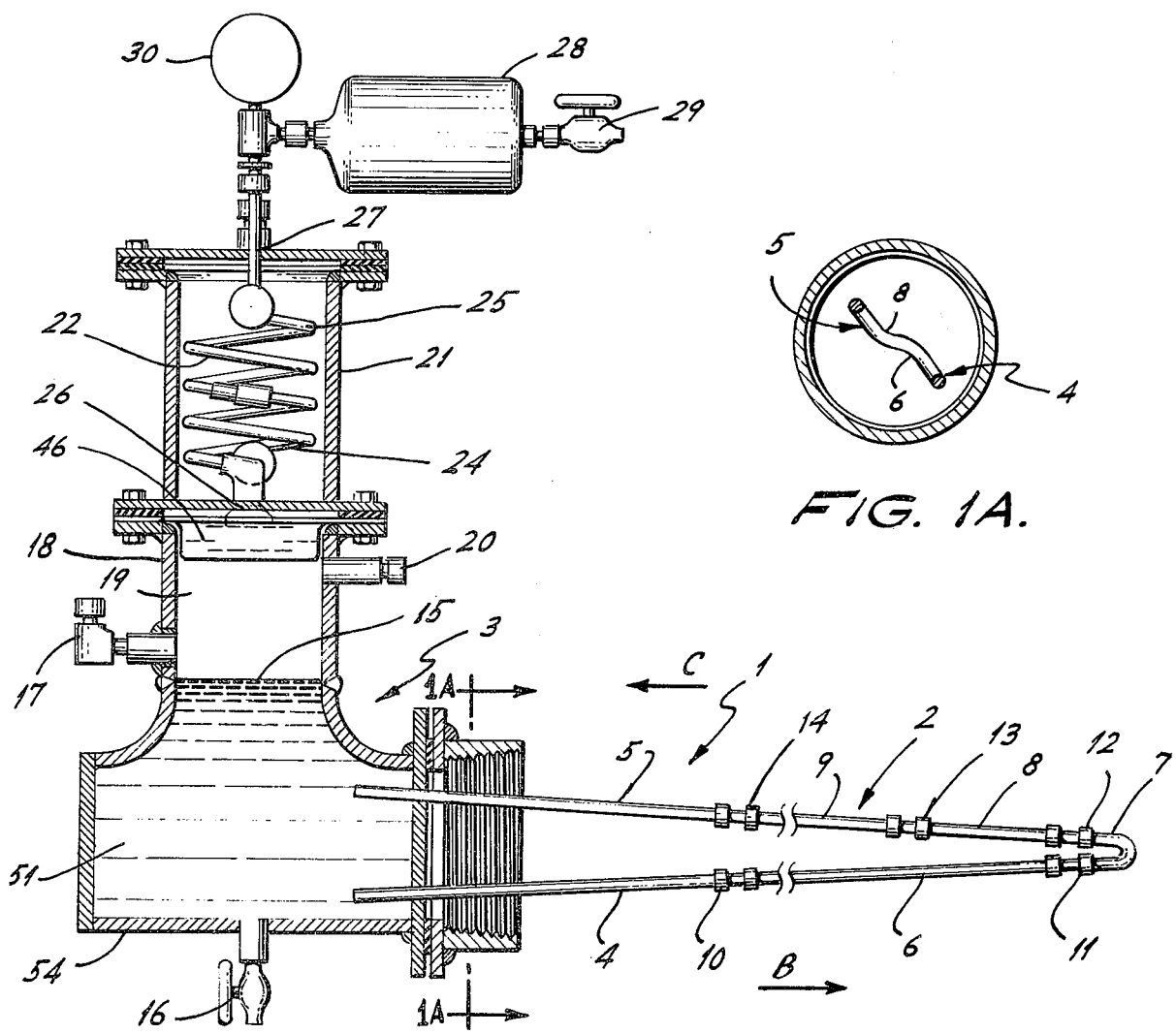
FIG. 1.
FIG. 1A.

CORROSION PROBE DEVICE FOR BOILER GASES

The present invention relates generally to apparatus for measuring deposition rates on surfaces and corrosion rates of surfaces in a flue gas system, and more particularly to a constant temperature cold-end corrosion probe for measuring the corrosion rate of a flue gas stream from a boiler burning sulfur-containing fuel.

Corrosion and deposition occur in the so called "cold end" of stack gas or flue gas systems. The flue gases contact relatively cold metal surfaces such as air preheaters and a heat exchanger where the heat of the flue gas is recovered to preheat furnace air. When the dew point temperature of the corrosive flue gases is realized, these gases condense (deposit) on the metal parts, thus causing corrosion. A particularly corrosive agent in the flue gas is sulfur-containing gas.

This corrosion can of course be controlled by using fuel additives which effectively lower the corrosive gas dew point. The beneficial effect of corrosion control treatments can be evaluated after a boiler has been shut down, for example, by simple inspection of the metal parts. Inherent drawbacks in this type of evaluation are required shutdown of the boiler and loss of metal parts already damaged.

In U.S. Pat. No. 3,861,876 a constant temperature corrosion probe system for determining corrosion in a boiler system is disclosed. Exemplary difficulties encountered in this system include difficulty in closely controlling the probe temperature and limited choice as to which cooling liquids can be used for a particular application.

The constant temperature cold-end corrosion probe of the present invention overcomes the problems heretofore known in determining useful deposition and corrosion rates for establishing an efficient and meaningful corrosion treatment program for a stack gas or flue gas system to enhance the life of the cold-end equipment. The device of the present invention includes a pipe loop probe insertable in the flue gas stream and connected to a coolant tank containing a coolant that will boil at the desired operating conditions. The operating pressure within the tank is controllable such that a series of boiling temperatures can be achieved for any given liquid coolant. A corrosion coupon (or test section) is removably mounted in the pipe loop and continually cooled by recirculation of the coolant from the tank. A water cooled condenser in the tank maintains the temperature of the coolant near the boiling temperature to provide a closer control of the loop temperature. A closed gas chamber in fluid flow communication with the condenser and coolant tank provides for a condenser with a variable heat transfer area to maintain a heat balance over the entire device, thus further enhancing the temperature control of the probe. Both legs of the pipe loop are inclined upwardly to provide a continuous passage for vapor bubbles to rise to achieve coolant circulation through the loop.

It is accordingly an object of the present invention to provide a new and improved device for determining the corrosion rate of metals in the cold end of a stack gas or flue gas system during operation of the system to evaluate a corrosion control treatment program.

Another object of the present invention is in the provision of a constant temperature cold-end corrosion probe device having a closer control over the temperature of the pipe loop.

Yet another object of the present invention relates to providing a constant temperature cold-end corrosion probe device which automatically maintains a heat balance over the entire device and in a unique manner.

A still further object of the present invention relates to providing a constant temperature cold-end corrosion probe device with a pipe loop designed to enhance the "natural" flow of coolant therethrough.

It is additionally an object of the present invention to provide a constant temperature cold-end corrosion probe device which is economical to operate.

Other objects, features and advantages of the present invention will be apparent from the following detailed disclosure, taken in conjunction with the accompanying drawings, wherein like reference numerals refer to like parts, in which:

FIG. 1 is an elevational view of the corrosion probe device according to the present invention;

FIG. 1A is a diagrammatic representation of the probe loop of the present invention as viewed along sight line A—A of FIG. 1;

FIG. 2 is a detailed elevational view of the shell of the condenser section of the corrosion probe device shown in FIG. 1;

Figure 3:
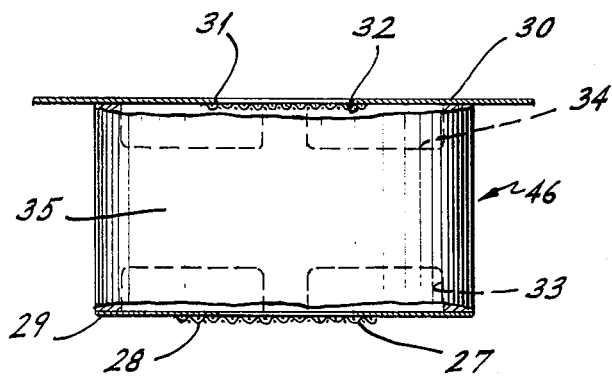
FIG. 3 is a detailed elevational view of the contact bed of the corrosion probe device of the present invention.

With reference to the drawings, and particularly to FIG. 1, the probe device of the present invention, generally designated by numeral 1, is adapted to be mounted at any place along the flue gas stream on the fireside of the boiler where the temperatures desired to be encountered are present. Particularly, the temperatures should be above the dew point of the corroding agent or above the maximum corroding temperature so that the probe, which includes a coupon, can be cooled to a temperature below the dew point of the corroding agent or to a temperature where maximum corrosion exists. The probe assembly of the present invention includes pipe loop 2 which, in use, extends within the boiler system (not shown) exposed to the flue gas stream. A coolant tank, generally designated 3, arranged outside the flue gas stream supplies coolant to pipe loop 2.

Pipe loop 2 includes upper and lower pipe sections 4 and 5, an outer pipe section 6, looped pipe section 7 and corrosion coupons 8 and 9. Of course, a single corrosion coupon could be used if desired. Sections 5, 8 and 9 define an upper coolant return run while sections 4 and 6 define a lower coolant supply run. As shown in FIG. 1, the ends of these runs are in fluid flow communication with the coolant tank 3. Elements 10, 11, 12, 13 and 14 are pipe couplings which can be manipulated in a well known manner to remove or insert the corrosion coupons. The liquid coolant 51 in the coolant tank 3 is kept at about its boiling point temperature. The pipe loop 2 is positioned so that the return run is located at a higher elevation than (above) the coolant supply run. As the coolant flows through pipe loop 2 in the direction of arrow B, the coolant absorbs heat from the hotter flue gas stream and begins to boil. As the coolant begins to boil, gaseous bubbles form, which bubbles will naturally tend to rise. The supply run and the return run are inclined upwardly in the direction of coolant flow through the pipe loop 2 such that the boiling process will actually urge the coolant flow along in the direction indicated by arrows B and C to form a "natural" flow of coolant. If the supply and return runs were maintained horizontally, a blanket of gaseous coolant would form along the upper inside walls of the pipe sections. Not only would such a vapor blanket hinder the natural flow of the coolant, but the vapor blanket would itself become superheated, causing temperature discrepancies about the circumferences of the pipe sections. As shown diagramatically in FIG. 1A, the return run and supply run are skewed with respect to the vertical plane.

The coolant tank 3 is designed to provide a liquid coolant reservoir 54 in a lower portion thereof. The numeral 15 indicates the level of liquid present in the tank 3. As will readily occur to the artisan, the coolant supply and return runs of the pipe loop 2 should be connected to the liquid coolant reservoir portion 54 of coolant tank 3 at a location below liquid coolant level 15. Element 16 designates a known drain valve for emptying the liquid coolant from the coolant tank 3. Element 17 is a known capped inlet connection for supplying liquid coolant to coolant tank 3. The upper portion 18 of coolant tank 3 defines a lower gas chamber 19 above the liquid coolant retained in reservoir 54. The liquid coolant 51 will boil off up into lower gas chamber 19. Element 20 is a pressure relief valve in fluid flow communication with lower gas chamber 19.

Located above lower gas chamber 19 is condenser chamber 21 which is shown in detail in FIG. 2. Connected in fluid flow communication with a wall of chamber 21 is a standard regulating valve and inlet pipe assembly 42 which is connected to a cold water supply. Also connected to the wall of condenser chamber 21 is a section of piping 43 which acts as a water outlet. Due to the location of outlet 43 above the regulating valve and inlet pipe assembly 42, a level of cooling water is established within condenser chamber 21. Located within condenser chamber 21 is a condenser coil 22 (shown in FIG. 1). The condenser coil 22 is comprised of upper condenser pipe section 25 which has a smaller diameter than lower condenser pipe section 24. The lower end of condenser coil 22 is in fluid flow communication with lower gas chamber 19. Thus, it can be seen that gaseous coolant which has boiled off from liquid coolant 51 will flow upwardly into the entrance 26 of condenser coil 22 which has been designed to permit free flow of gaseous coolant upward and free flow of condensed liquid coolant downward.

Located adjacent to and below the condenser entrance 26 is a contact bed 46 which may be of any known design. For purposes of illustration a detailed contact bed suitable for use with the present probe device is shown in FIG. 3. At the lower end of contact bed 46 is a plate 29, for example a metal plate, through which flow opening 27 is provided. Similarly, at the upper end of contact bed 46 a plate 30 having a flow opening 31 is provided. Both of these flow openings are covered with a mesh screen, such as a stainless steel 10–20 mesh screen. Elements 33 and 34 are typical bubble caps which redirect the flow of fluid therethrough. If desired, the space 35 between bubble caps 33 and 34 can be filled with packing such as irregular gravel (not shown). Additionally, a baffle (not shown) having the configuration of a flat washer (disk with a hole in it) for enhancing gas-liquid contact in the bed could be placed across gas flow path through space 35. Thus, it will readily occur to the artisan, having the benefit of the present disclosure, that gaseous coolant moving upwardly from the coolant reservoir 54 will enter contact bed 46 through lower flow opening 27 and will intimately contact condensed coolant moving downwardly from condenser coil 22 through upper flow opening 31. The contact bed is designed so that sufficient heat transfer occurs between the vapor and liquid so that the temperature of the liquid in the reservoir 54 will be increased to that of the condensate in the reservoir. This is a further measure to achieve stability and closer temperature control in the probe assembly.

The upper end of condenser coil 22 is connected to an upper gas chamber 28 which, preferably, contains an inert, pressurized gas in use. In fluid flow communication with upper gas chamber 28 is pressure gauge 30. Element 29 is a vent valve which permits bleeding off gas from the upper gas chamber. Since upper gas chamber 28 is in fluid flow communication with condenser coil 22, which, in turn, is in fluid flow communication with lower gas chamber 19, upper gas chamber 28 is in fluid flow communication with lower gas chamber 19. It will readily occur to the artisan, having the benefit of the present disclosure, that the boiling point temperature of the liquid coolant will vary with changes in pressure in the gas chambers. Thus, the pressure condition in upper gas chamber 28 can be manipulated, for example, by valve 29, to vary the gas pressure in the system, so that the boiling point temperature of the liquid coolant will be varied. Accordingly, a single liquid coolant can be used to provide a wide range of controlled temperatures within the probe assembly.

Figure 4:
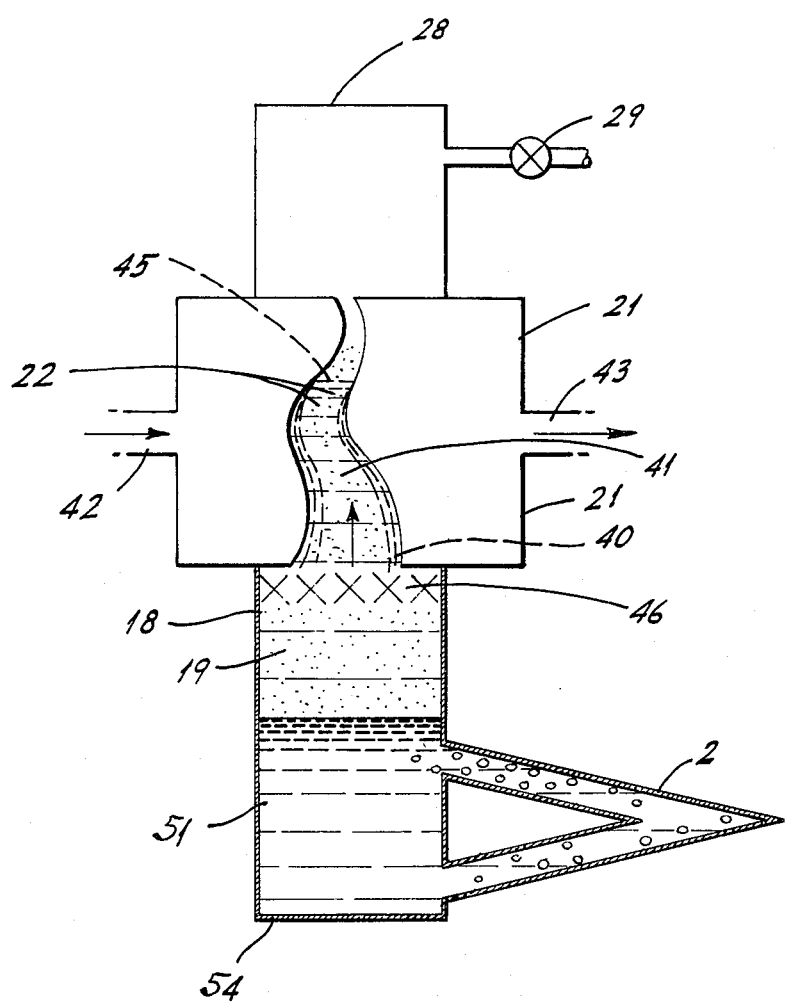
FIG. 4 is a schematic illustration of the probe device in operation.

It is desirable to maintain the same boiling temperature and corresponding probe loop temperature regardless of the temperature of the flue gases, their velocity, specific heat, etc. To maintain a heat balance over the entire probe assembly, it is necessary that the same amount of heat be discharged in the cooling water as is absorbed from the flue gases. This could be accomplished, with a constant heat transfer area in the condenser by adjusting the rate of cooling water continuously according to the heat load and as the temperature of the cooling water may vary. According to an additional feature of the present invention the probe device is designed so that the area for heat transfer utilized varies to continuously correspond to that necessary to achieve a heat balance, regardless of the temperature difference between the cooling water and the desired boiling point temperature of the coolant, preferably an organic solvent. With particular reference to FIG. 4, this is accomplished by the combination of upper gas chamber 28, the condensing coil 22 having an excess of heat transfer area, and the contact bed 46. The gaseous coolant is condensed on the tube side of condenser coil 22 and cooling water flows on the shell side of the condenser coil at a rate at least large enough to achieve a heat balance. The heat transfer area on the tube side of condenser coil 22 is at least as large as necessary to achieve heat balance and is so designed as to permit free flow of coolant vapor upward in the middle area of the coil 22, as generally indicated by reference number 41, and free flow of condensed liquid coolant downward along the inner coil wall, as generally indicated by reference numeral 40. The volume of the condenser coil 22 on the tube side should be small as compared to the volumes of the upper gas chamber 28 and lower gas chamber 19. During operation of the probe device, upper gas chamber 28 contains an inert gas under pressure. Air has been found to be useful as such inert gas. Thus, inert gas and coolant vapor will be present in the upper section of the condenser coil 22 in a proportion corresponding to their partial pressures at the cooling water temperature. Only coolant vapor and liquid coolant will be present in the lower section of the condenser coil. Thus, some middle portion of the condenser coil 22 will be a zone of transition 45 from the conditions occurring in the lower section to those occurring in the upper section. As heat input increases, this transition zone 45 automatically moves upward in the condenser coil 22, increasing the effective area of heat transfer until heat being removed by the cooling water again equals the heat being extracted at the pipe loop 2.

Having thus described the probe assembly of the present invention, an exemplary operation will be described with particular reference to FIG. 1 and FIG. 4. A liquid coolant, preferably an organic liquid such as trichloroethylene, is delivered through inlet connection 17 into coolant tank 3 to fill the liquid coolant reservoir portion 54 thereof. Coolant vapor and air fill the upper and lower gas chambers 28 and 19. The total pressure is atmospheric and the temperature is ambient, e.g., 25°C. Vent valve 29 is closed and pipe loop 2 is inserted in a hot gas stream to be tested. The regulating valve 42 is turned to the desired open position to start the flow of cooling water. Heat flows into the liquid coolant and the liquid coolant temperature and pressure increase. Coolant vapor and air move upward from lower gas chamber 19 through condenser coil 22, with all vapor being condensed to lower gas chamber 19. An equilibrium condition is established when boiling of the liquid coolant occurs. All air has been removed from lower gas chamber 19 to upper gas chamber 28 and the pressure in the apparatus will be established by the relative volumes of the upper and lower gas chambers. For example, if the lower gas chamber has twice the volume of the upper gas chamber, it will be appreciated that forcing the air from the lower to the upper gas chamber will increase the pressure of air in the upper chamber to a given value. The temperature in the upper gas chamber will be the same as that of the cooling water and the temperature in the lower gas chamber will be about the boiling temperature of the liquid coolant corresponding to the system pressure. Contact bed 46 provides intimate contact of coolant vapor moving upward and condensed liquid coolant moving downward. The contact bed is designed according to known principles, so that sufficient heat transfer occurs between the vapor and liquid to ensure that the liquid coolant temperature is increased to that of boiling liquid in the reservoir 54.

As explained above, by virtue of the condenser coil with a variable heat transfer area, the temperature in the coolant tank 3 will remain the same regardless of changes in the rate of heat injection into pipe loop 2.

To change the operating temperature, vent valve 29 is cracked open to permit escape of a portion of air (or other vent gas), then closed. Some coolant vapor may also be removed but in an insignificant amount. The apparatus will now operate at an equilibrium corresponding to some lower pressure and at the boiling temperature of the coolant. Of course, it should be appreciated that an inverse change in the operating temperature could be accomplished by supplying air (or other vent gas) to gas chamber 28.

The apparatus can be vented to the condition where it is operating at a pressure the same as the environment (approximately 1 atmosphere absolute). The vent normally will be closed to prevent gradual diffusion and loss of coolant vapor to the environment.

It will be understood that modifications and variations may be effected without departing from the scope of the present invention and that this application is to be limited only by the scope of the appended claims.

The invention is hereby claimed as follows:

1. A constant temperature cold-end corrosion probe device for the flue gas stream of a boiler, said device comprising:
   constant temperature probe means for insertion into said flue gas stream, and
   temperature maintaining means for maintaining the temperature of said probe means substantially constant,
   wherein said temperature maintaining means includes condenser means having a variable tube side heat transfer area.

2. A constant temperature cold-end corrosion probe device according to claim 1, wherein said probe means comprises fluid flow loop means having fluid supply run means and fluid return run means, said loop means being adapted for installation in the flue gas stream and including corrosion coupon means, and wherein said temperature maintaining means comprises tank means in fluid flow communication with said loop means, said tank means being adapted to contain a level of liquid coolant in use for flow through said loop means.

3. A constant temperature cold-end corrosion probe device according to claim 2, wherein said coupon means is removable.

4. A constant temperature cold-end corrosion probe device according to claim 2, wherein both said fluid supply run means and said fluid return run means are inclined upwardly in the direction of coolant flow therethrough in use.

5. A constant temperature cold-end corrosion probe device according to claim 2, wherein said fluid return run means is located above said fluid supply run means.

6. A constant temperature cold-end corrosion probe device according to claim 2, wherein said condenser means comprises:
   a first condenser end in fluid flow communication with said tank means and a second condenser end in fluid flow communication with variable pressure gas supply means.

7. A constant temperature cold-end corrosion probe device according to claim 6, wherein said condenser means comprises coiled pipe means arranged vertically above said liquid coolant in said tank means.

8. A constant temperature cold-end corrosion probe device according to claim 7, wherein said condenser means is provided within a closed chamber through which cooling fluid flows in contact with said condenser means.

9. A constant temperature cold-end corrosion probe device according to claim 8, wherein said condenser means is in fluid flow communication with said variable pressure gas supply means through said second condenser end and is in fluid flow communication with said tank means through said first condenser end, and wherein said first condenser end is arranged below said second condenser end.

10. A constant temperature cold-end corrosion probe device according to claim 9, wherein said first condenser end is connected in fluid flow communication with contact bed means.

11. A constant temperature cold-end corrosion probe device according to claim 10, wherein said fluid return run means is located above said fluid supply run means.

12. A constant temperature cold-end corrosion probe device according to claim 6, wherein said first condenser end is spaced above said level of liquid coolant to define first gas chamber means within said tank means between said level of liquid coolant and said first condenser end.

13. A constant temperature cold-end corrosion probe device according to claim 12, wherein contact bed means are provided within said first gas chamber means in fluid flow communication with said first condenser end such that in use condensed liquid coolant flows from said condenser means through said first condenser end and through said contact bed means to contact boiled-off gaseous coolant flowing from said liquid coolant in said tank means through said contact bed toward said first condenser end.

14. A constant temperature cold-end corrosion probe device according to claim 12, wherein said fluid return run means is located above said fluid supply run means.

15. A constant temperature cold-end corrosion probe device according to claim 12, wherein said variable pressure gas supply means comprises:
a closed gas reservoir having valve means and a given gas volume to define second gas chamber means.

16. A constant temperature cold-end corrosion probe device according to claim 15, wherein said first gas chamber means has a gas volume which is larger than said given gas volume.

17. A constant temperature cold-end corrosion probe device according to claim 15, wherein said fluid return run means is located above said fluid supply run means.

18. A constant temperature cold-end corrosion probe device for the flue gas stream of a boiler, said device comprising:
constant temperature probe means for insertion into said flue gas stream,
temperature maintaining means for maintaining the temperature of said probe means substantially constant, and
pressure varying means for varying the temperature of said probe means.

19. A constant temperature cold-end corrosion probe device according to claim 18, wherein said coolant supply run is located below said coolant return run.

20. A constant temperature cold-end corrosion probe device according to claim 18, wherein said constant temperature probe means comprises coolant flow loop means having a coolant supply run and a coolant return run, said loop means being adapted for installation in the flue gas stream and including corrosion coupon means, wherein said temperature maintaining means comprises coolant tank means in fluid flow communication with said flow loop means for supplying coolant thereto through said supply and return run means, said tank means having a lower liquid coolant reservoir containing liquid coolant and having an upper first gas chamber means above said liquid coolant for gaseous coolant which has boiled off from the liquid coolant, and wherein said pressure varying means is in fluid flow communication with said gas chamber means for varying the pressure within said gas chamber means.

21. A constant temperature cold-end corrosion probe device according to claim 20, wherein said coolant supply run and said coolant return run are inclined upwardly in the direction of coolant flow therethrough.

22. A constant temperature cold-end corrosion probe device according to claim 20, wherein said pressure varying means comprises second gas chamber means.

23. A constant temperature cold-end corrosion probe device according to claim 22, wherein said coolant supply run is located below said coolant return run.

24. A constant temperature cold-end corrosion probe device for the flue gas stream of a boiler, said device comprising:
probe means for inserting into said flue gas stream, said probe means comprising coolant flow loop means having coolant supply run means and coolant return run means, and
temperature maintaining means for maintaining the temperature of said probe means substantially constant,
wherein said coolant supply run means and said coolant return run means are inclined upwardly in the direction of coolant flow therethrough.

25. A constant temperature cold-end corrosion probe device according to claim 24, wherein said temperature maintaining means comprises coolant tank means in fluid flow communication with an end of each of said coolant supply run means and said coolant return run means, said coolant tank containing liquid coolant in use at a level above both of said ends.

26. A constant temperature cold-end corrosion probe device according to claim 25, wherein said coolant supply run means and said coolant return run means are continuously inclined.

27. A constant temperature cold-end corrosion probe device for the flue gas stream of a boiler, said device comprising:
coolant flow loop means having coolant supply run means and coolant return run means, said loop means being adapted for installation in the flue gas stream and including corrosion coupon means,
coolant tank means in fluid flow communication with said loop means, said tank means containing a level of liquid coolant for flow through said loop means and defining above said liquid coolant level gas chamber means for containing gaseous coolant which has boiled off from said liquid coolant,
condenser means in fluid flow communication with said gas chamber means for receiving and condensing said gaseous coolant from said gas chamber means, and
contact bed means located between said gas chamber means and said condenser means for contacting said gaseous coolant from said gas chamber means with condensed liquid coolant from said condenser means.

28. A constant temperature cold-end corrosion probe device according to claim 27, wherein said coolant return run means is located above said coolant supply run means.

* * * * *